(12) United States Patent
Shih et al.

(10) Patent No.: US 8,696,752 B2
(45) Date of Patent: Apr. 15, 2014

(54) INTERBODY CAGE FOR SPINE FUSION

(75) Inventors: Wei-Jen Shih, Kaohsiung (TW); Yu-Ting Lyu, Kaohsiung (TW); Wei-Te Chen, Kaohsiung (TW); Yen-Nien Chen, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 81 days.

(21) Appl. No.: 13/340,842

(22) Filed: Dec. 30, 2011

(65) Prior Publication Data

US 2013/0173000 A1 Jul. 4, 2013

(51) Int. Cl.
*A61F 2/44* (2006.01)

(52) U.S. Cl.
USPC ............................ 623/17.16; 623/17.13

(58) Field of Classification Search
USPC ......... 623/17.13, 17.15, 17.16; 606/248, 249, 606/254–257, 283–285, 90; 267/42–47, 267/133, 140.3, 158–160, 163–165, 181, 267/182, 244, 260, 261; 29/96.9–896.938
See application file for complete search history.

(56) References Cited

U.S. PATENT DOCUMENTS

| | | | | | |
|---|---|---|---|---|---|
| 150,804 | A | * | 5/1874 | Vose | 267/47 |
| 266,842 | A | * | 10/1882 | Kitzmiller | 267/42 |
| 398,156 | A | * | 2/1889 | Hayes | 267/42 |
| 517,106 | A | * | 3/1894 | Laass | 267/42 |
| 603,028 | A | * | 4/1898 | Pell et al. | 267/261 |
| 2,009,496 | A | * | 7/1935 | Johnson | 76/104.1 |
| 3,389,902 | A | * | 6/1968 | Young | 267/159 |
| 3,671,030 | A | * | 6/1972 | Marion | 267/270 |
| 5,417,602 | A | * | 5/1995 | McGraw | 446/48 |
| 5,522,753 | A | * | 6/1996 | McGraw | 446/36 |
| 5,676,702 | A | * | 10/1997 | Ratron | 623/17.16 |
| 5,749,916 | A | * | 5/1998 | Richelsoph | 623/17.16 |
| 5,785,303 | A | * | 7/1998 | Kutschi | 267/103 |
| 5,976,187 | A | * | 11/1999 | Richelsoph | 623/17.16 |
| 6,170,808 | B1 | * | 1/2001 | Kutschi | 267/107 |
| 6,231,609 | B1 | * | 5/2001 | Mehdizadeh | 623/17.11 |
| 6,572,653 | B1 | * | 6/2003 | Simonson | 623/17.13 |
| 6,770,096 | B2 | | 8/2004 | Bolger et al. | |
| 7,867,276 | B2 | * | 1/2011 | Matge et al. | 623/17.11 |
| 8,118,873 | B2 | * | 2/2012 | Humphreys et al. | 623/17.16 |
| 8,262,068 | B1 | * | 9/2012 | Monson et al. | 267/292 |
| 8,465,008 | B2 | * | 6/2013 | Beer et al. | 267/160 |
| 8,523,944 | B2 | * | 9/2013 | Jimenez et al. | 623/17.15 |
| 8,529,628 | B2 | * | 9/2013 | Marino et al. | 623/17.16 |
| 8,540,452 | B2 | * | 9/2013 | Jimenez et al. | 403/220 |
| 2003/0160396 | A1 | * | 8/2003 | Dean | 277/628 |

(Continued)

FOREIGN PATENT DOCUMENTS

TW M333884 U 6/2008

*Primary Examiner* — Michael T Schaper
(74) *Attorney, Agent, or Firm* — Alan Kamrath; Kamrath IP Lawfirm, P.A.

(57) ABSTRACT

An interbody cage includes a substrate having a plurality of curve slits, with each of the curve slits having a plurality of sections. A plurality of deformable ribs is formed, with each deformable rib between any adjacent two of the curve slits and having a first end and a second end. The first and second ends of each deformable rib respectively connect with two opposite lateral bars of the substrate, and a plurality of folds is formed on the plurality of deformable ribs in places adapted to be bent. In use, any adjacent two of the deformable ribs are capable of being bent to depart from each other to define a filling room.

14 Claims, 6 Drawing Sheets

(56) References Cited

U.S. PATENT DOCUMENTS

| | | | |
|---|---|---|---|
| 2005/0038515 A1* | 2/2005 | Kunzler | 623/17.13 |
| 2005/0240269 A1* | 10/2005 | Lambrecht et al. | 623/17.13 |
| 2005/0267471 A1* | 12/2005 | Biedermann et al. | 606/61 |
| 2006/0004455 A1* | 1/2006 | Leonard et al. | 623/17.15 |
| 2007/0191953 A1* | 8/2007 | Trieu | 623/17.15 |
| 2007/0191958 A1* | 8/2007 | Abdou | 623/17.16 |
| 2007/0219634 A1* | 9/2007 | Greenhalgh et al. | 623/17.16 |
| 2007/0293949 A1 | 12/2007 | Salerni et al. | |
| 2008/0167686 A1* | 7/2008 | Trieu et al. | 606/249 |
| 2008/0177389 A1* | 7/2008 | Parrish | 623/17.16 |
| 2008/0183204 A1* | 7/2008 | Greenhalgh et al. | 606/198 |
| 2009/0062916 A1* | 3/2009 | Fox et al. | 623/17.16 |
| 2009/0138088 A1* | 5/2009 | Scribner et al. | 623/17.16 |
| 2010/0004748 A1* | 1/2010 | Cordaro | 623/17.16 |
| 2010/0131009 A1* | 5/2010 | Roebling et al. | 606/249 |
| 2010/0292799 A1* | 11/2010 | Hansell et al. | 623/17.15 |
| 2011/0196495 A1* | 8/2011 | Hunt | 623/17.16 |
| 2012/0025576 A1* | 2/2012 | Stern et al. | 297/344.1 |
| 2012/0203346 A1* | 8/2012 | Kraus | 623/17.16 |
| 2012/0265306 A1* | 10/2012 | Trieu | 623/17.16 |
| 2012/0318574 A1* | 12/2012 | Beer et al. | 174/75 F |
| 2013/0023990 A1* | 1/2013 | Zipnick et al. | 623/17.16 |
| 2013/0053963 A1* | 2/2013 | Davenport | 623/17.16 |
| 2013/0166030 A1* | 6/2013 | Biedermann et al. | 623/17.16 |

* cited by examiner

INTERBODY CAGE FOR SPINE FUSION

BACKGROUND OF THE INVENTION

1. Field of the Invention

The present invention relates to an interbody cage and, more particularly, to an interbody cage for spine fusion, which is capable of enhancing the growing speed and stability of bones as well as an easy 2D-to-3D conversion in structure.

2. Description of the Related Art

Recently, cases of spinal diseases have occurred often, since the numbers of office workers and elders are increasing, and spinal diseases are common in these two groups. Therefore, how to take care of patients of spinal diseases has become more and more important.

Generally, medical attention of a spinal patient after an operation is extremely important for the patient's recovery, and the patient usually has to put on a spinal brace for a long time so that the spinal brace may provide an external support for the spine of the patient and prevent the recovering spine from injury again.

Nowadays, the way to improve the patient's recovery is to implant an interbody cage in a position adjacent to a bone defect in his spine, with filler such as Calcium Phosphate, bone graft, and auto-genous graft in the interbody cage. However, the filler inside the interbody cage may easily flow away due to intrusion of soft tissues, which usually grow faster than bone tissues, in the interbody cage or circulatory system if the meshes of the interbody cage are not well designed. Thus, this implant made of the interbody cage and filler will not achieve a desirable performance.

Figure 1:
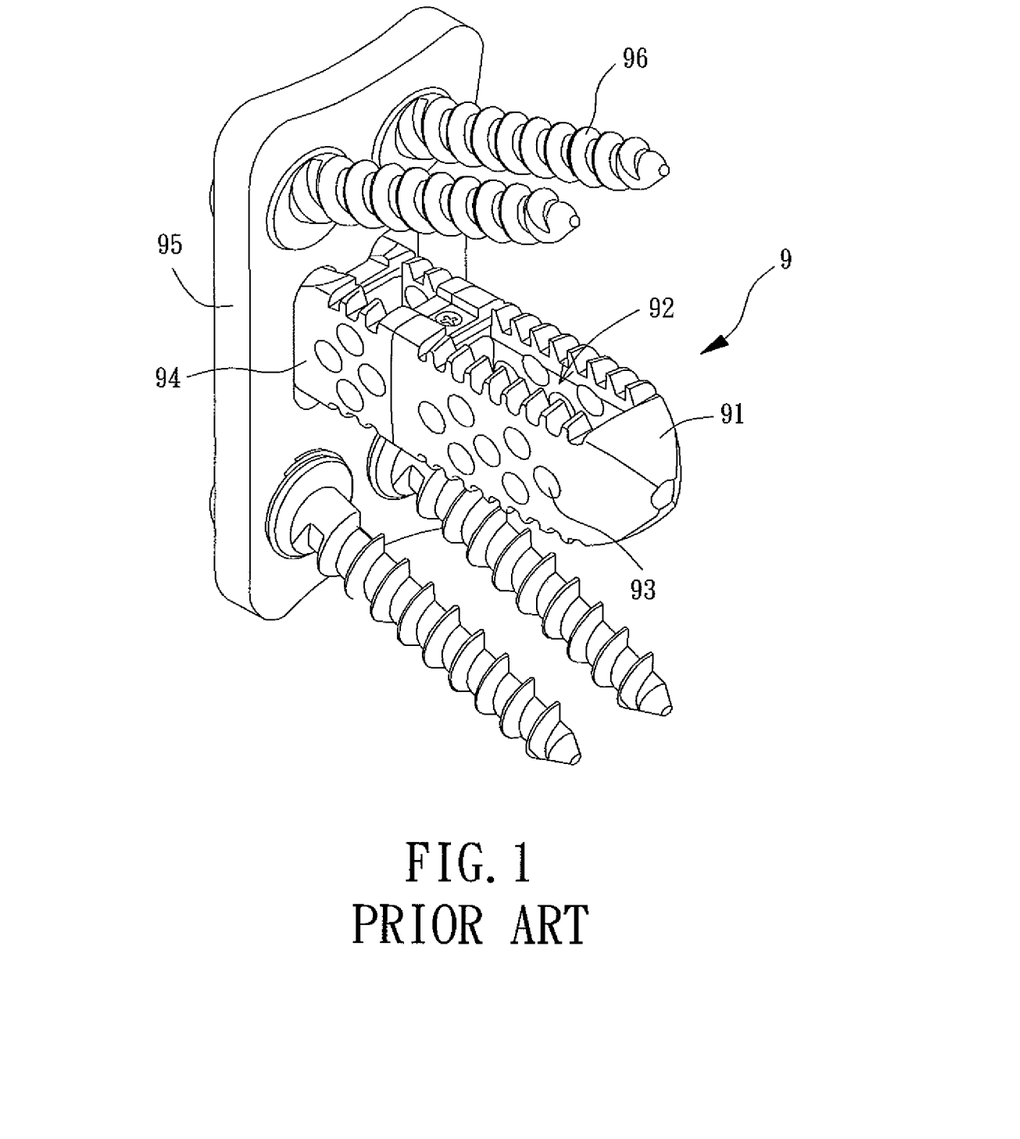
FIG. 1 shows a perspective view of a conventional interbody cage.

Referring to FIG. 1, a conventional interbody cage 9 disclosed by Taiwan Patent No. of M333884 is shown. The interbody cage 9 has a head 91 on the front side thereof, a room 92 formed behind the head 91, a plurality of holes 93 arranged in lateral walls of the interbody cage 9 and communicating with the room 92, a base 94 on the rear side of the interbody cage 9, and a fixing seat 95 for the base 94 to firmly mount on. The room 92 is arranged for insertion of the filler, and the filler inside the interbody cage 9 is accessible to the bone cells of a spine through the holes 93 for spine fusion.

However, there should be a plurality of screws 96 coupling with the fixing seat 95 to firmly position the interbody cage 9 in a position adjacent to a bone defect. Futher, this conventional interbody cage 9 is suitable to be positioned between two vertebral columns only. Moreover, the complexity, difficulty in manufacture and manufacture cost of this conventional interbody cage 9 are high, since the interbody cage 9 can only be shaped by 3D laser carving and spark-discharge forming. Additionally, in a medical operation, this complex interbody cage 9 also leads to a long time period in assembly of the screws 96 and the fixing seat 95. Thus, the possibility of bacterial infection in the medical operation can be largely raised.

Furthermore, the filler loss problem due to soft tissues' intrusion and to the circulatory system may easily occur in this interbody cage 9, since the room 92 and holes 93 are not particularly designed to block the intruded soft tissues and the filler inside the room 92. Accordingly, the conventional interbody cage 9 cannot effectively enhance the growing speed of a defective bone but only serves as a support. Thus, the interbody cage 9 cannot help a lot in recovery of the bone.

Therefore, a titanium-based interbody cage for enhancing the growing speed and stability of defective bones and suitable for use in any part of the spine is needed to solve the above problems.

SUMMARY OF THE INVENTION

It is therefore the primary objective of this invention to provide an interbody cage with a simple and integral structure without any joint between any two separate members and capable of an easy 2D-to-3D conversion in structure, to lower the difficulty and cost in manufacture and to avoid undesirable deformation.

Another objective of this invention is providing an interbody cage to release stress at ends of a deformable rib to avoid an undesirable break.

Still another objective of this invention is providing an interbody cage to prevent the soft tissues from intrusion and to surely hold the filler to avoid the flowing away.

Still another objective of this invention is providing an interbody cage suitable to be used in any position of a patient with spinal disease for enhancing the growing of the bone tissues via the filler inside this interbody cage.

The invention discloses an interbody cage including a substrate. The substrate has a plurality of curve slits, with each of the curve slits having a plurality of sections. A plurality of deformable ribs is formed, with each deformable rib between any adjacent two of the curve slits and having a first end and a second end. The first and second ends of each deformable rib respectively connect with two opposite lateral bars of the substrate, and a plurality of folds is formed on the plurality of deformable ribs in places adapted to be bent.

The invention further discloses that each deformable rib has a narrow part and a wide part, with a plurality of through holes formed in the wide part and penetrating the substrate.

The invention further discloses that a plurality of end holes is formed at ends of the curve slits and penetrates the substrate.

The invention further discloses that the plurality of folds is line depressions in the substrate and parallel to the lateral bars.

The invention further discloses that a part of the folds is arranged on one side of the deformable ribs in the narrow parts forming the first ends or second ends, and the other part of the folds is arranged on another side of the deformable ribs in the wide parts forming the first ends or second ends.

The invention further discloses that a thickness of the substrate is 20-200 micrometers and that widths of the folds are in a range between 0.1-0.3 mm.

The invention further discloses that diameters of the through holes are in a range between 1-3 mm.

The invention further discloses that a biodegradable macromolecular film is formed on one side of the substrate to totally or partially cover the one side.

The invention further discloses that each section of any one of the curve slits has a first part and a second part in arc shapes. The first parts and the second parts of the sections of any one of the curve slits are arranged in a staggered manner. Curvature centers of the first parts are on one side of the curve slit, and curvature centers of the second parts are on the other side of the curve slit.

The invention further discloses that each narrow part of any one of the deformable ribs is formed between a first part and a second part of adjacent two of the curve slits defining the deformable rib, with centers of the said first and second parts being bent towards each other. Each wide part of any one of the deformable ribs is formed between a first part and a second part of adjacent two of the curve slits defining the deformable rib, with centers of the said first and second parts being bent away from each other.

The invention further discloses that the wide parts are in a circular shape and that the through holes in the wide parts are in a circular shape concentric to the circular shape of the wide parts.

The invention further discloses that the wide parts are in an eye-like shape and that the through holes in the wide parts are also in an eye-like shape.

The invention further discloses that the wide parts are in a circular shape. A part of the wide parts has the through holes in a circular shape, and the other part of the wide parts has the through holes in a bar shape. The wide parts having the circular through holes and the wide parts having the bar-shaped through holes are arranged in a staggered manner.

The invention further discloses that each first part is in an S shape and that each second part is in an arc shape.

The invention further discloses that the narrow part of one of the deformable ribs is in an S shape and that the wide part of the deformable rib is in a circle shape, with a circular through hole formed in the wide part and concentric to the circular shape of the wide part.

The invention further discloses that the wide parts are in a rhombus shape and that the through holes in the wide parts are formed in an ellipse shape.

The invention further discloses that the wide parts are in a rectangle shape and that the through holes in the wide parts are formed in an oval shape.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first," "second," and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 2:
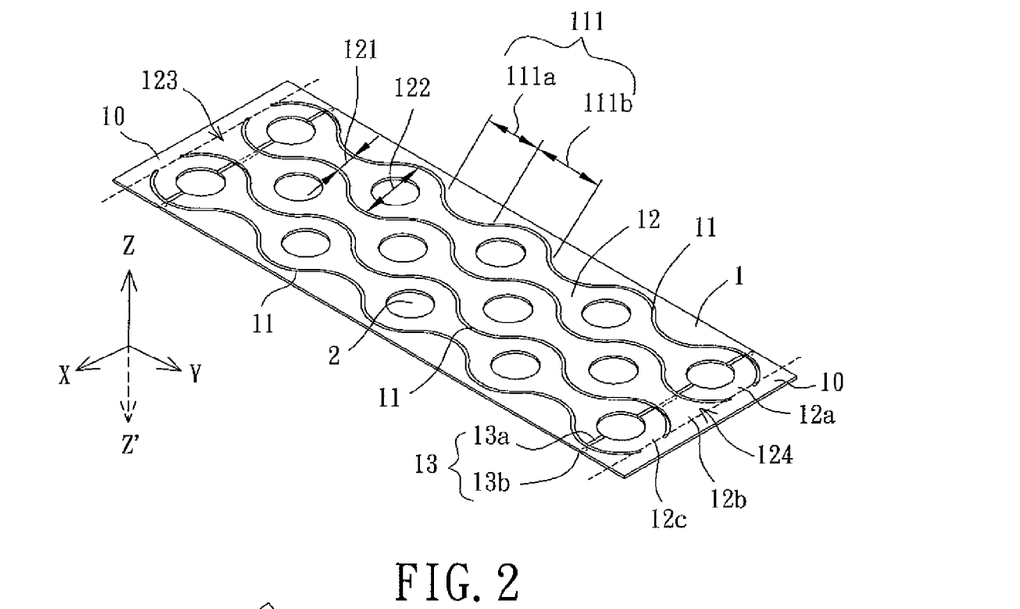
FIG. 2 shows a perspective view of an interbody cage according to a preferable embodiment of the invention in a 2D flat piece form.

FIG. 2 shows an interbody cage according to a preferable embodiment of the invention, which includes a substrate 1 preferably made of pure titanium or titanium alloy with a thickness of 20-200 micrometers between two opposite sides of the substrate 1. Thus, the substrate 1 is easy to be converted into a specific shape during a medical operation.

The substrate 1 has two lateral bars 10 on two opposite ends of the substrate 1 and a plurality of curve slits 11 extending between the two lateral bars 10. Each of the curve slits 11 has a plurality of sections 111. Routes of the curve slits 11 in the sections 111 may be the same or different to form the sections 111 with repeated or random shapes. Specifically, each slit 11 of the substrate 1 in the present example shown by FIGS. 2 and 3 has continuous and repeated sections 111. However, routes of the curve slits 11 are not limited thereto, while various examples of the curve slit 11 are shown in FIGS. 4-8 and illustrated later.

Referring to FIG. 2 again, each section 111 of any one of the curve slits 11 has a first part 111a and a second part 111b. The first parts 111a and the second parts 111b of the sections 111 of the same curve slit 11 are arranged in a staggered manner. Particularly, it is preferable that both of the first part 111a and the second part 111b are in arc shapes, curvature centers of the first parts 111a are on one side of the curve slit 11, and curvature centers of the second parts 111b are on the other side of the curve slit 11, so that each curve slit 11 is in a S-shape. Preferably, each curve slit 11 extends from one of the lateral bars 10 to the other one of the lateral bars 10 and is spaced from two opposite edges of the substrate 1 by the lateral bars 10. For example, as those shown in FIG. 2, each curve slit 11 extends from one of the lateral bars 10 close to a left edge to the other lateral bar 10 close to a right edge in a Y direction.

Figure 3:
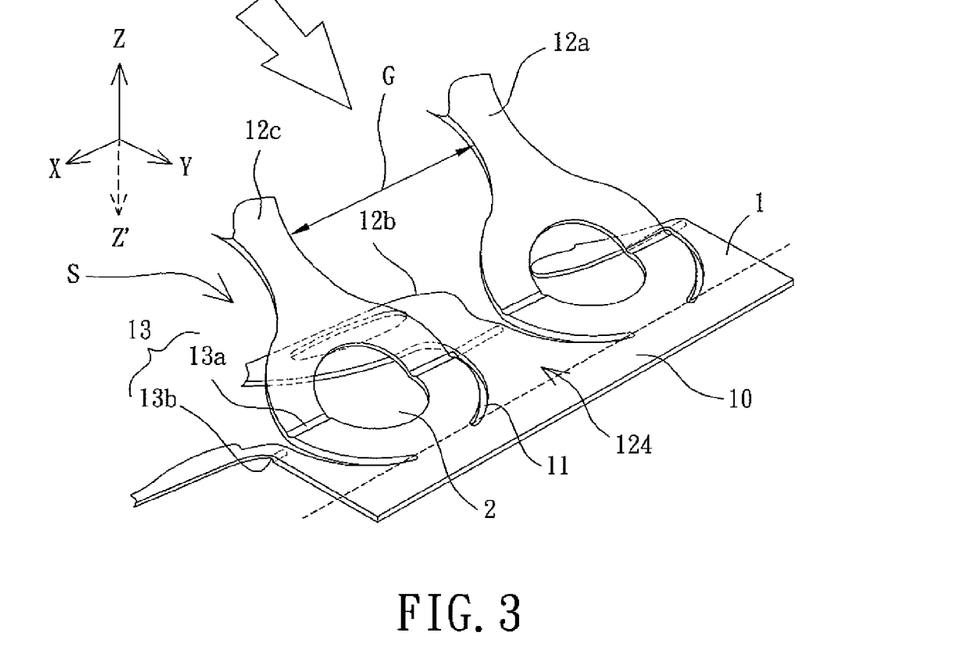
FIG. 3 shows a perspective view of the interbody cage in a 3D cage form.

Referring to FIGS. 2 and 3, there is a deformable rib 12 between any two curve slits 11, so that the deformable rib 12 is bent while two external forces oppositely press the substrate 1 on the two lateral bars 10 in directions parallel to the Y direction as the arrows shown in FIG. 3. Therefore, the deformable ribs 12 can be bent, with any two adjacent deformable ribs 12 being bent in directions parallel to a Z direction perpendicular to the Y direction to depart from each other. Thus, the substrate 1 is converted from a 2D flat piece into an integral 3D cage without any joint between any two separate members. In this embodiment, each deformable rib 12 has a plurality of narrow parts 121 and a plurality of wide parts 122. Each narrow part 121 of a deformable rib 12 is formed between a first part 111a and a second part 111b of two adjacent curve slits 11 defining the deformable rib 12, and centers of the first and second parts 111a, 111b are bent towards each other. Contrarily, although each wide part 122 of the deformable rib 12 is also formed between a first part 111a and a second part 111b of two adjacent curve slits 11 defining the deformable rib 12, centers of the first and second parts 111a, 111b are bent away from each other. In correspondence with the arrangement of the first parts 111a and second parts 111b of the curve slits 11, the narrow parts 121 and wide parts 122 may also be arranged in a staggered manner.

Moreover, a first end 123 and a second end 124 of the deformable rib 12 are defined. The first and second ends 123, 124 respectively connect with the two lateral bars 10 extending in a X direction perpendicular to the Y and Z directions. The first and second ends 123, 124 can be bent relative to the lateral bars 10 of the deformable rib 12 while the external pressure enforces the two lateral bars 10 to get close, to form the 3D cage capable of receiving the filler.

Additionally, the substrate 1 further has a plurality of folds 13 formed on at least one of the sides of the substrate 1 in places to be bent to convert the 2D flat piece into the 3D cage. In this embodiment, the plurality of folds 13 is formed on the deformable ribs 12 and adjacent to the first and second ends 123, 124. According to the user's need, the folds 13 may be formed on one side of the substrate 1 only or formed on both of the opposite sides of the substrate 1, and the folds 13 may be formed adjacent to only one of the first and second ends 123, 124 or formed adjacent to both of the first and second ends 123, 124. Each of the folds 13 is a line depression in the substrate 1, with the widths of the folds 13 in a range between 0.1-0.3 mm for the face of the deformable ribs 12 with a fold 13 to be easily bent. Thus, the deformable ribs 12 can be guided to spread out in designed directions.

Please refer to FIG. 2, again. In this embodiment, in order to spread out the deformable ribs 12 in a staggered manner, that is, to bend any two adjacent deformable ribs 12 oppositely, a part of the folds 13 are arranged on one side of the deformable ribs 12 in the narrow parts 121 forming the first ends 123 or second ends 124, and the other part of the folds 13 are arranged on the other side of the deformable ribs 12 in the wide parts 122 forming the first ends 123 or second ends 124. Namely, if a deformable rib 12 is designed to be bent in an upward direction with one of the folds 13 labeled as "13a" and formed on an upper side of this deformable rib 12 in the wide part 122 forming the second end 124 of this deformable rib 12, another deformable rib 12 next to the above deformable rib 12 and designed to be bent in a downward direction can have another one of the folds 13 labeled as "13b" and formed on a bottom side of this another deformable rib 12 in the narrow part 121 forming the second end 124 of this another deformable rib 12. Preferably, the folds 13a, 13b are parallel to the lateral bars 10 and aligned with each other. In other words, a side of a deformable rib 12 having a fold 13 is designed to face in the direction in which the deformable rib 12 is bent towards. Specifically, in accordance with the showing of FIG. 3, taking three of the deformable ribs 12, which are particularly labeled as "12a," "12b" and "12c," for example, the folds 13a are formed on the upper sides of the deformable ribs 12a, 12c in the wide parts 122 thereof for the deformable ribs 12a, 12c to bend upwards in the Z direction. However, the fold 13b is formed on the bottom side of the deformable rib 12b in the narrow part 121 thereof, since the deformable rib 12b has to bent downwards in a Z' direction opposite to the Z direction. Accordingly, when the external forces are applied to the lateral bars 10, the folds 13 can focus the external forces for the deformable ribs 12 to be bent in predetermined directions. Thus the substrate 1 may be surely converted into the desired 3D cage. Please notice that the above structure is merely disclosed for illustration, and the arrangement of the folds 13 is not limited but can be change according to the user's need.

The interbody cage according to the preferable embodiment of the invention can further have a plurality of through holes 2, with the plurality of through holes 2 penetrating the substrate 1 from one of the two opposite sides to the other one of them, to communicate these two opposite sides of the substrate 1. Particularly, the plurality of through holes 2 is formed in the wide parts 122 of the deformable rid 12 and may connect with the curve slit 11 if necessary. In the example shown in FIGS. 2 and 3, each one of the through holes 2 is in the shape of a circle and arranged in a respect one of the wide parts 122, with the curvature centers of the first part 111a and second part 111b defining any one of the wide parts 122 and with the center of the through hole 2 in this wide part 122 being the same. In this example, the diameters of the through holes 2 are in a range between 0.5-3.5 mm, preferably in a range between 1-3 mm, and more preferably of 2 mm, to lighten the substrate 1, to improve the flexibility of the substrate 1, and to lower the interference due to the 3D cage on X-ray films.

Figure 9:
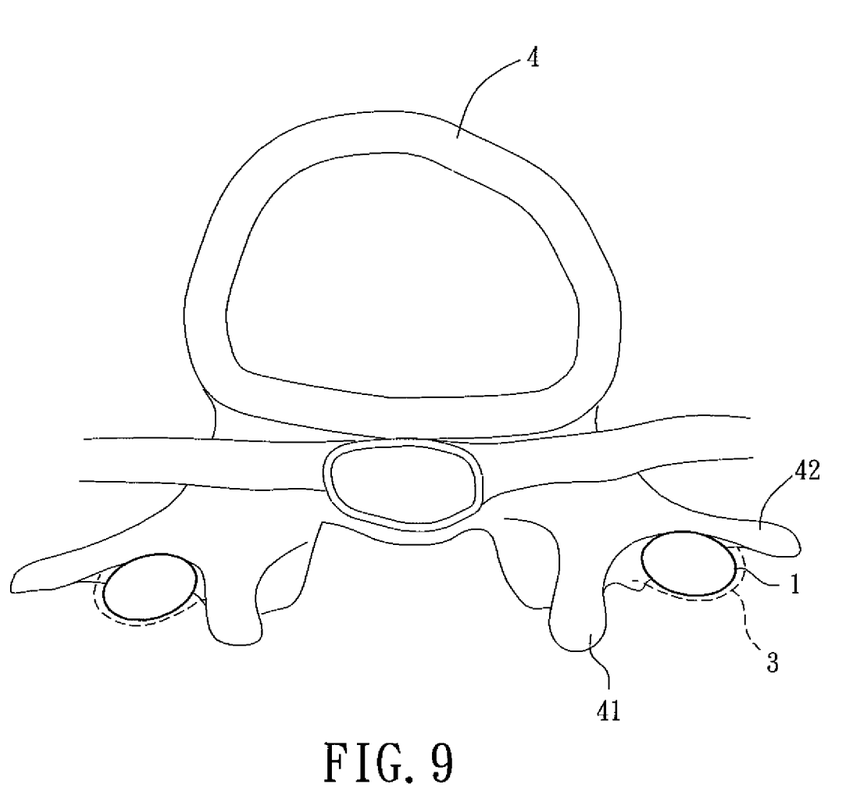
FIG. 9 shows a sketch diagram of the interbody cage in use.

Referring to FIG. 9, a biodegradable macromolecular film 3 can be formed on one side of the substrate 1, which may totally or partially cover the one side. Preferably, the biodegradable macromolecular film 3 covers one side of the substrate 1 only, with the uncovered side of the substrate 1 facing the bone defect for the filler inside the 3D cage to enhance the growing of the bone tissues and with the covered side of the substrate 1 capable of preventing the intrusion of the soft tissues. The biodegradable macromolecular film 3 may be made of collagen, chitosan, gelatin or hyaluronan.

The interbody cage of the present invention can be made by the following method: selecting a titanium film with 50 micrometers as the substrate 1; forming the plurality of curve slits 11 and through holes 2 with the previous discussed structures by 2D laser carving; forming the fold 13 with a width of 0.2 mm by laser processing; and soaking the carved substrate 1 into 37% hydrochloric acid for 30 minutes to lower the roughness of the surfaces of the substrate 1 to a degree smaller than 1.5 micrometers.

When the interbody cage of this invention is used, the substrate 1 has to be transformed from the 2D flat piece into the integral 3D cage. Referring to FIG. 3, the lateral bars 10 are moved toward each other by external forces in the direction parallel to the Y direction and shown by the arrows. Thus the deformable ribs 12a, 12b, 12c, which are originally aligned side by side to form the 2D flat piece, can be departed from each other to form the 3D cage. Specifically, the first and second ends 123, 124 of the deformable ribs 12a, 12c serve as hinges, and the folds 13a focus the external forces for the deformable rib 12a, 12c to easily bend in the Z direction corresponding to the folds 13a. The first and second ends 123, 124 of the deformable rib 12b serve as hinges, and the folds 13b focus the external forces for the deformable rib 12b to bend in the Z' direction corresponding to the folds 13b. Therefore, the oppositely bent deformable ribs 12a, 12b can define a filling room "S" for receiving the filler. It should be noticed that a number of the deformable ribs 12 is changeable to adjust the length of the interbody cage upon need. It is preferable that the length of the interbody cage is that of 2-3 vertebral columns of the patient.

Particularly, a gap "G" is formed between two adjacent deformable ribs 12a or two adjacent deformable ribs 12b, which are on the same side of the filling room "S," and is in a shape identical to that of a deformable rib 12b or a deformable rib 12a since the filling room "S" is formed by the oppositely bent deformable ribs 12a, 12b. Once the filler is filled into the filling room "S" in use, the filler is accessible to the bone tissues via the gap "G." As a result, it is preferable that the width of the wide part 122 is smaller than that of the filler, with the width of the wide part 122 being 1.5-4.5 mm and more preferably being 2-4 mm, Thus the filler is firmly held inside the filling room "S" and cannot fall out of the interbody cage through the gap "G" to effectively enhance the recovery of the bone defect.

Referring to FIGS. 4-8, the interbody cages of the preferable embodiment of this invention with various curve slits 11 and through holes 2 having different shapes are shown. It should be noticed that the arrangements of the curve slits 11 and through holes 2 can be adjusted to improve the strength and smoothness of the bent deformable ribs 12. Thus, the deformable ribs 12 will not be easily broken or hurt the bone tissues nearby via sharp corners thereof.

Figure 4:
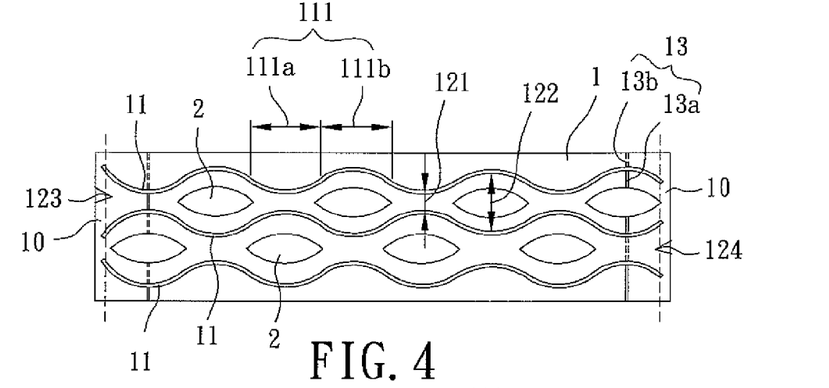
FIGS. 4-8 show top views of various interbody cages according to the preferable embodiment of the invention.
Figure 5:
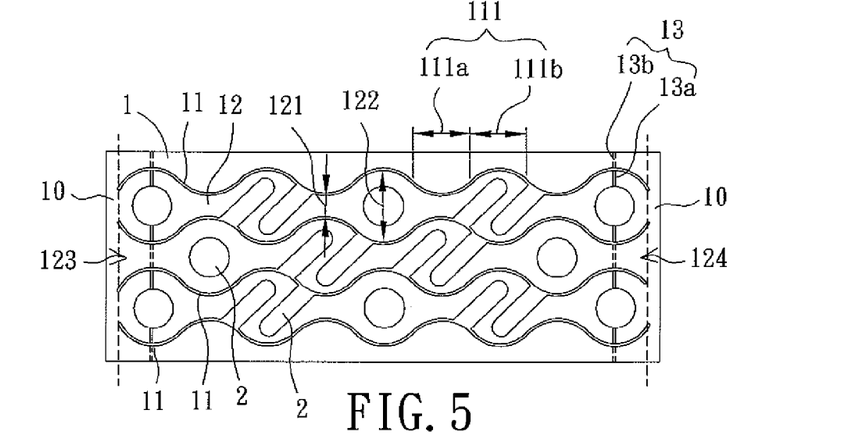
Figure 6:
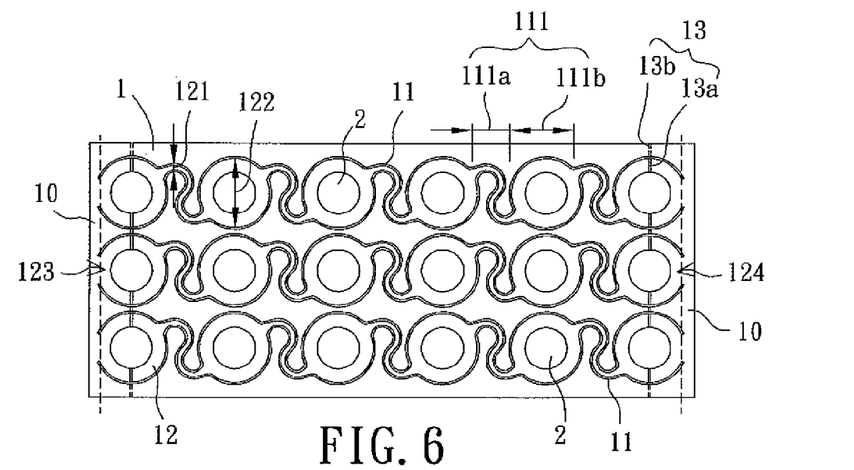
Figure 7:
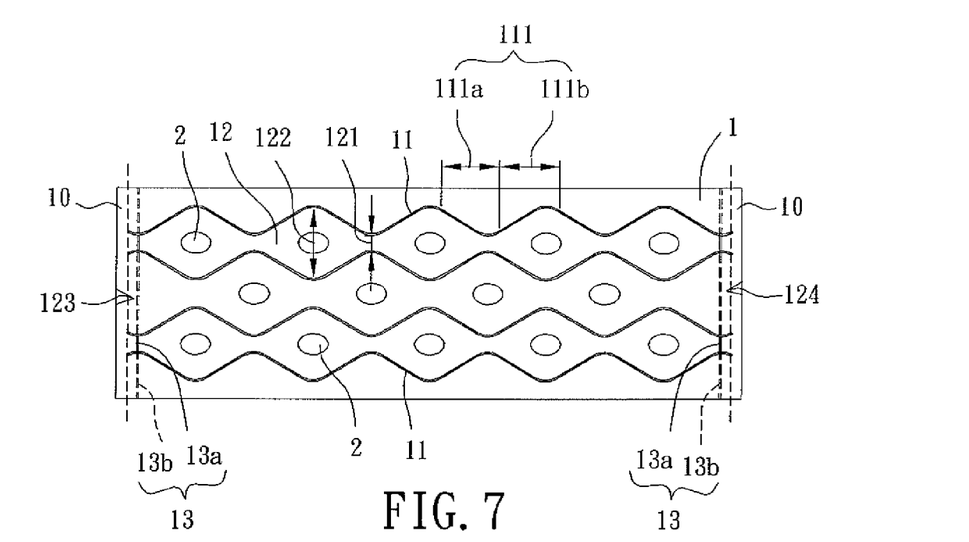
Figure 8:
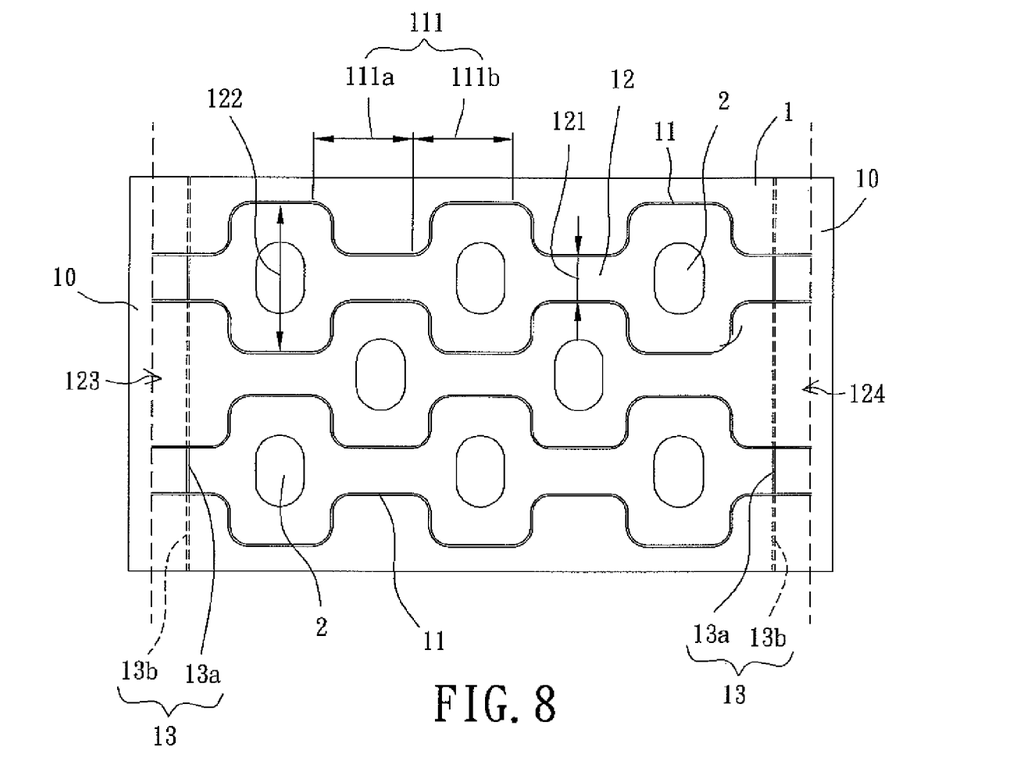

Referring to FIG. 4, the first part 111a and second part 111b defining any one of the wide parts 122 are arranged to form the wide part 122 into an eye-like shape, while the through holes 2 in the wide parts 122 are also correspondingly formed in an eye-like shape. Referring to FIG. 5, the first part 111a and second part 111b defining any one of the wide parts 122 are arranged to form the wide part 122 into a circle. A part of the wide parts 122 has the through holes 2 in a circular shape, and the other part of the wide parts 122 has the through holes 2 in a bar shape. Preferably, the wide parts 122 having the circular through holes 2 and wide parts 122 having the bar-shaped through holes 2, which are the wide parts 122 of the same deformable rib 12, are arranged in a staggered manner. Referring to FIG. 6, the first parts 111a are in an S shape, and the second parts 111b are in an arc shape. Thus, the narrow part 121 of a deformable rib 12 is in an S shape, and the wide part 122 is in a circular shape with a circular through hole 2 formed in the wide part 122. Referring to FIG. 7, the first part 111a and second part 111b defining any one of the wide parts 122 are arranged to form the wide part 122 into a rhombus shape, while the through holes 2 in the wide parts 122 are formed in an ellipse shape. Referring to FIG. 7, first part 111a and second part 111b defining any one of the wide parts 122 are arranged to form the wide part 122 into a rectangle shape, while the through holes 2 in the wide parts 122 are formed in an oval shape. The above illustrated examples are shown for illustration but do not limit the practice of this invention.

Referring to FIG. 9, when the interbody cage of the present invention is used in a medical operation, the filler is initially filled into the filling room "S" formed by the bent deformable ribs 12b of the pressed substrate 1. Then, the interbody cage with the filler may be disposed in a suitable position near the bone defect directly or by thread without any nail for fixing the interbody cage. The suitable position is preferably between the cervical spine 41 and the transverse spine 42 of the spine 4 of the patient.

Figure 10:
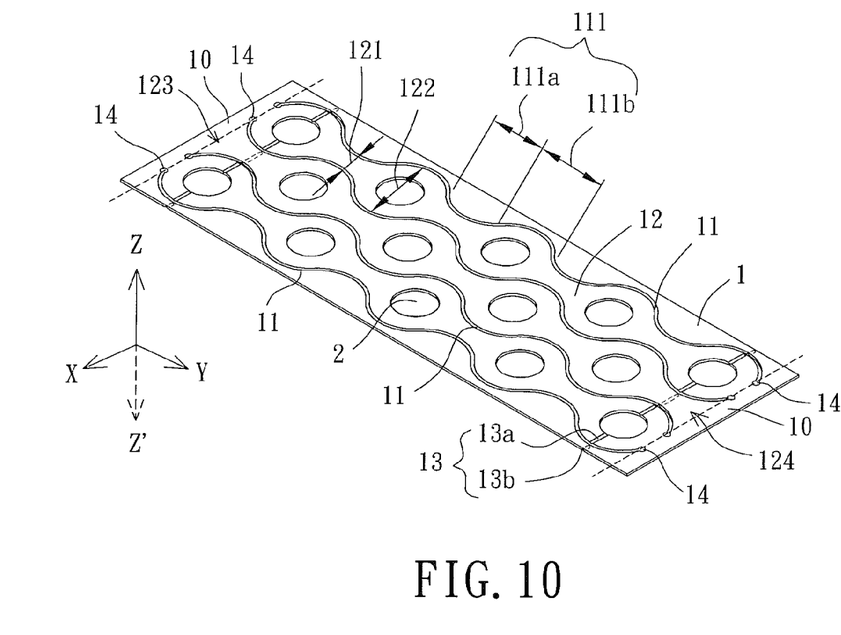
FIG. 10 shows a perspective view of an interbody cage according to another preferable embodiment of the invention with end holes in a 2D flat piece form.
Figure 11:
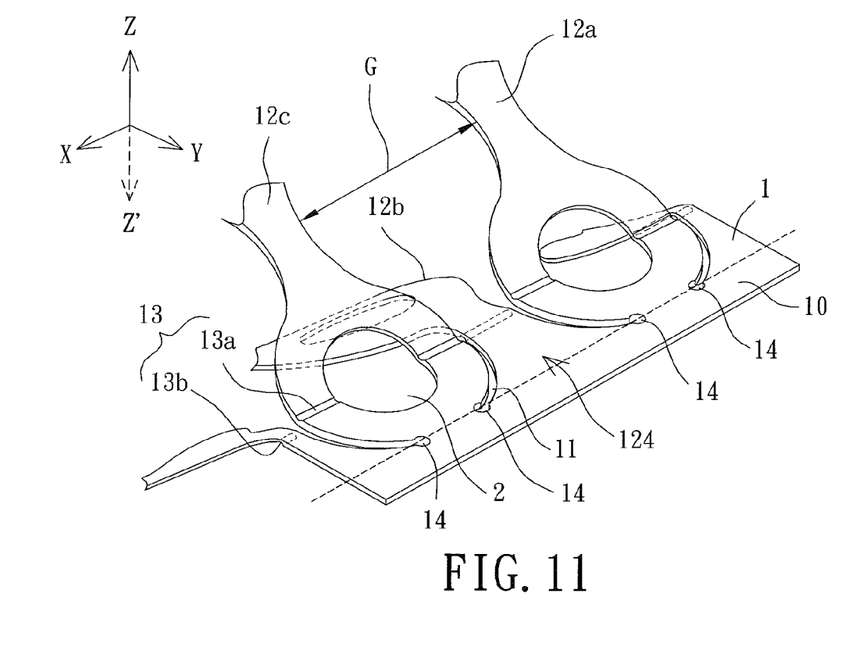
FIG. 11 shows a perspective view of the interbody cage with end holes in a 3D cage form.

In addition to the above disclosed structures, another embodiment is shown by FIGS. 10 and 11. In this embodiment, a plurality of end holes 14 formed at ends of the curve slits 11 is provided, with the end holes 14 also penetrating the substrate 1 from one of the two opposite sides to the other one of the two opposite sides. With these end holes 14, the external forces deforming the deformable ribs 12 will not tear the lateral bars 10 from the ends of the curve slits 11. Thus, damage to or an undesirable break in the lateral bars 10 is avoided. Specifically, each end hole 14 communicates with the respect curve slit 11, and there are preferably two end holes 14 at two ends of one curve slit 11. Preferably, each end hole 14 has a bore larger than a width of the curve slit 11 communicated therewith, and the end hole 14 is in the shape of a circle.

In sum, the interbody cage of the present invention is characterized in the following features. First, the interbody cage is easy for storage before use, since the substrate 1 is a 2D flat piece. Second, the interbody cage is convenient for use, since the deformable ribs 12 can be spread out easily by opposite external forces on the lateral bars 10 to form the 3D cage. Third, the external forces applied to the lateral bars 10 may focus on the folds 13 guiding the deformable ribs 12 to bend in designed directions in a staggered manner. Thus, the folds 13 can prevent any deformable rib 12 from an undesirable deformation. Fourth, the interbody cage is strong, since the substrate 1 is integrally formed without any joint between any two separate members. Thus, the structure of the interbody cage will not be loosened or broken from the joint. Fifth, the end holes 14 can release the stress at the first and second ends 123, 124 of the deformable ribs 12 to avoid a break of the deformable ribs 12 or the lateral bars 10. Sixth, the routes of the curve slits 11 can be designed to avoid weak points of the deformable ribs 12 and to avoid hurt to the bone. Finally, the interbody cage has a reduced weight, improved flexibility and lower interference on X-ray films, since the through holes 2 are formed in the deformable rids 12. Thereby, the present interbody cage not only can be manufactured easily, but can efficiently hold the filler as well as efficiently prevent the soft tissues from intrusion via the applied biodegradable macromolecular film 3. Accordingly, the present interbody cage can provide a sufficient strength for support as well as improve the growing of the bone tissues.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. An interbody cage comprising:
a substrate having a plurality of curve slits, with each of the plurality of curve slits having a plurality of sections, wherein a plurality of deformable ribs is formed, with each of the plurality of deformable ribs being between any adjacent two of the plurality of curve slits and having a first end and a second end, wherein the first and second ends of each of the plurality of deformable ribs respectively connect with two opposite lateral bars of the substrate, with a plurality of folds formed on the plurality of deformable ribs in places adapted to be bent, wherein each of the plurality of deformable ribs has a narrow part and a wide part, with a plurality of through holes formed in the wide parts and penetrating the substrate, wherein each of the plurality of sections of any one of the plurality of curve slits has a first part and a second part in arc shapes, wherein the first parts and the second parts of the plurality of sections of said any one of the curve slits are arranged in a staggered manner, wherein curvature centers of the first parts are on one side of said any one of the curve slits, and wherein curvature centers of the second parts are on another side of said any one of the curve slits.

2. The interbody cage as claimed in claim 1, wherein a part of the plurality of folds is arranged on one side of the plurality of deformable ribs in the narrow parts forming the first ends or the second ends, and wherein another part of the plurality of folds is arranged on another side of the plurality of deformable ribs in the wide parts forming the first ends or the second ends.

3. The interbody cage as claimed in claim 1, wherein each narrow part of any one of the plurality of deformable ribs is formed between the first part and the second part of adjacent two of the plurality of curve slits defusing said any one of the plurality of deformable ribs, and wherein each wide part of said any one of the plurality of deformable ribs is formed between the first part and the second part of adjacent two of the plurality of curve slits defining said any one of the plurality of deformable ribs.

4. The interbody cage as claimed in claim 1, wherein the wide parts are in a rhombus shape, and wherein the plurality of through holes in the wide parts are formed in an ellipse shape.

5. The interbody cage as claimed in claim 1, wherein the wide parts are in a rectangle shape, and wherein the plurality of through holes in the wide parts are formed in an oval shape.

6. An interbody cage comprising:
a substrate having a plurality of curve slits, with each of the plurality of curve slits being of a fluctuating shape defining a plurality of sections each having first and second parts, wherein a plurality of deformable ribs is formed by the plurality of curve slits, with each deformable rib being between any adjacent two of the plurality of curve slits and having a first end and a second end, wherein the first and second ends of each deformable rib respectively connect with two opposite lateral bars of the substrate, wherein each deformable rib has multiple narrow parts and multiple wide parts between the first and second ends, with a plurality of through holes formed in the multiple wide parts and penetrating the substrate, wherein the first and second parts are in arc shapes, wherein curvature centers of the arc shapes of the first parts are on one side of any one of the plurality of curve slits, and wherein curvature centers of the arc shapes of the second parts are on another side of the any one of the plurality of curve slits.

7. The interbody cage as claimed in claim 6, wherein each narrow part of any one of the plurality of deformable ribs is formed between one of the first parts and a corresponding second part of the any adjacent two of the plurality of curve slits, and with each wide part of any one of the plurality of deformable ribs is formed between another one of the first parts and a corresponding second part of the any adjacent two of the plurality of curve slits.

8. The interbody cage as claimed in claim 7, wherein the wide parts are in a circular shape, and wherein each through hole in the wide parts is in a circular shape concentric to the circular shape of the wide parts.

9. The interbody cage as claimed in claim 7, wherein the wide parts are in an eye-like shape, and wherein each through hole in the wide parts is also in an eye-like shape.

10. The interbody cage as claimed in claim 7, wherein the wide parts are in a circular shape, with some of the plurality of through holes being in a circular shape, with others of the plurality of through holes being in a bar shape, and with the wide parts having the circular through holes and the wide parts having the bar-shaped through holes are arranged in a staggered manner.

11. The interbody cage as claimed in claim 6, wherein each first part is in an S shape and each second part is in an arc shape.

12. The interbody cage as claimed in claim 6, wherein each wide part is in a rhombus shape, and wherein each through hole is in an ellipse shape.

13. The interbody cage as claimed in claim 6, wherein each wide part is in a rectangle shape, and wherein each through hole is in an oval shape.

14. An interbody cage comprising:
   a substrate having a plurality of curve slits, with each of the plurality of curve slits being of a fluctuating shape defining a plurality of sections each having first and second parts, wherein a plurality of deformable ribs is formed by the plurality of curve slits, with each deformable rib being between any adjacent two of the plurality of curve slits and having a first end and a second end, wherein the first and second ends of each deformable rib respectively connect with two opposite lateral bars of the substrate,
   wherein each deformable rib has multiple narrow parts and multiple wide parts between the first and second ends, with a plurality of through holes formed in the multiple wide parts and penetrating the substrate,
   wherein each first part is in an S shape and each second part is in an arc shape, wherein each narrow part of one of the plurality of deformable ribs is in an S shape and each wide part of the one of the plurality of deformable ribs is in a circle shape, with each through hole being circular and concentric to the circular shape.

* * * * *